US009278123B2

(12) United States Patent
Sauerberg et al.

(10) Patent No.: US 9,278,123 B2
(45) Date of Patent: Mar. 8, 2016

(54) SOLID COMPOSITIONS COMPRISING A GLP-1 AGONIST AND A SALT OF N-(8-(2-HYDROXYBENZOYL)AMINO) CAPRYLIC ACID

(75) Inventors: Per Sauerberg, Farum (DK); Simon Bjerregaard, Hilleroed (DK); Flemming Seier Nielsen, Roskilde (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/994,262

(22) PCT Filed: Dec. 16, 2011

(86) PCT No.: PCT/EP2011/073060
§ 371 (c)(1),
(2), (4) Date: Sep. 16, 2013

(87) PCT Pub. No.: WO2012/080471
PCT Pub. Date: Jun. 21, 2012

(65) Prior Publication Data
US 2013/0345134 A1  Dec. 26, 2013

Related U.S. Application Data

(60) Provisional application No. 61/425,087, filed on Dec. 20, 2010.

(30) Foreign Application Priority Data

Dec. 16, 2010  (EP) .................................... 10195285

(51) Int. Cl.
*A61K 9/20* (2006.01)
*A61K 38/26* (2006.01)
*A61P 3/04* (2006.01)
*A61P 3/10* (2006.01)

(52) U.S. Cl.
CPC .............. *A61K 38/26* (2013.01); *A61K 9/2013* (2013.01); *A61K 9/2077* (2013.01)

(58) Field of Classification Search
CPC ............ A61K 9/20; A61K 38/26; A61P 3/04; A61P 3/10
See application file for complete search history.

(56) References Cited

U.S. PATENT DOCUMENTS

| | | | |
|---|---|---|---|
| 5,773,647 A | 6/1998 | Leone-Bay et al. | |
| 5,866,536 A | 2/1999 | Leone-Bay et al. | |
| 7,049,283 B2 | 5/2006 | Ault et al. | |
| 8,039,018 B2 | 10/2011 | Majuru et al. | |
| 8,053,429 B2 | 11/2011 | Cumming et al. | |
| 2005/0009748 A1 | 1/2005 | Dinh et al. | |
| 2005/0148497 A1 | 7/2005 | Khan | |
| 2007/0049557 A1 | 3/2007 | Ahmed et al. | |
| 2007/0224262 A1 | 9/2007 | Majuru et al. | |
| 2008/0153779 A1 | 6/2008 | Liao et al. | |
| 2009/0124639 A1 | 5/2009 | Oyewumi et al. | |
| 2009/0156478 A1* | 6/2009 | Lau et al. ........................ 514/12 |
| 2010/0210526 A1 | 8/2010 | Joshi | |
| 2011/0142800 A1 | 6/2011 | Kidron et al. | |
| 2011/0218148 A1 | 9/2011 | Azria et al. | |
| 2015/0150811 A1 | 6/2015 | Jensen et al. | |

FOREIGN PATENT DOCUMENTS

| | | |
|---|---|---|
| CN | 101010339 A | 8/2007 |
| WO | 0048589 A1 | 8/2000 |
| WO | 0050012 A1 | 8/2000 |
| WO | 0141737 A2 | 6/2001 |
| WO | 03005944 A1 | 1/2003 |
| WO | 2005004900 A1 | 1/2005 |
| WO | 2005107773 A2 | 11/2005 |
| WO | 2006/097537 A2 | 9/2006 |
| WO | 2006103661 A2 | 10/2006 |
| WO | 2006124047 A2 | 11/2006 |
| WO | 2007117706 A2 | 10/2007 |
| WO | 2007146234 A2 | 12/2007 |
| WO | 2008020096 A1 | 2/2008 |
| WO | 2008039351 A2 | 4/2008 |
| WO | 2008109385 A2 | 9/2008 |
| WO | 2009032749 A2 | 3/2009 |
| WO | 2009/050738 A2 | 4/2009 |
| WO | 2010/020978 A1 | 2/2010 |
| WO | 2010/092163 A2 | 8/2010 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2012080471 A1 | 6/2012 |

OTHER PUBLICATIONS

Beglinger et al., "Pharmacokinetics and pharmacodynamic effects of oral GLP-1 and PYY3-36: A proof of concept study in healthy subjects," Clin. Pharma. Therap. 84: 468-474 (2008)).*
Beglinger C et al., Clinical Pharmacology and Therapeutics,"Pharmacokinetics and Pharmacodynamic Effects of Oral GLP-1 and PYY3-36: A Proof-of-Concept Study in Healthy Subject"., 2008, vol. 84, No. 4, pp. 468-474.
Steinert RE et al, American Journal of Clinical Nutrition,"Oral Administration of Glucagon-like Peptide 1 or Peptide YY 3-36 Affects Food Intake in Healthy Male Subjects", 2010, vol. 92, pp. 810-817.
Steinert RE et al., Clinical Pharmacology and Therapeutics,"Orally Administered Glucagon-like Peptide-1 Affects Glucose Homeostasis Following an Oral Glucose Tolerance Test in Healthy Male Subjects", 2009, vol. 86, No. 6, pp. 644-650.
He Xiaorong et al., Mechanistic Study of the Effect of Roller Compaction and Lubricant on Tablet Mechanical Strength, Journal: Journal of Pharmaceutical Sciences,Year: 2007, vol. 96, No. 5, pp. 1342-1355.
Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.
Rowe Raymond C et al., Book: Handbook of Pharmaceutical Excipients, Title: Acesulfame Potassium, Edition—5th, Year: 2006, Complete book.
Steinert R E et al., Orally Administered Glucagon-Like Peptide-1 Affects Glucose Homeostasis Following an Oral Glucose Tolerance Test in Healthy Male Subjects, Journal: Clinical Pharmacology and Therapeutics, Year: 2009, vol. 86, No. 6, pp. 644-650.

(Continued)

*Primary Examiner* — Julie Ha
*Assistant Examiner* — Kristina M Hellman
(74) *Attorney, Agent, or Firm* — Richard W. Bork

(57) ABSTRACT

The present invention relates to solid compositions comprising a GLP-1 agonist and a salt of N-(8-(2-hydroxybenzoyl) amino)caprylic acid and their use in medicine.

19 Claims, No Drawings

(56) References Cited

OTHER PUBLICATIONS von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.

Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year: 2008. vol. 84, No. 4, pp. 468-474.

Leonard Thomas W et al., Promoting absorption of drugs in humans using medium-chain fatty acid-based solid dosage forms:GIPET™, Journal: Expert Opinion Drug Delivery, Year: 2006, vol. 3(5), pp. 685-692.

Maher Sam et al., Overcoming poor permeability: translating permeation enhancers for oral peptide delivery, Journal: Drug Discovery Today:Technologies, Year: 2011, vol. 9, No. 2, pp. e113-e119.

Maher Sam et al., Safety and efficacy of sodium caprate in promoting oral drug absorption: from in vitro to the clinic, Journal: Advanced Drug Delivery Reviews, Year: 2009, vol. 61, pp. 1427-1449.

Michel Marre et al., GLP-1 receptor agonists today, Journal: Diabetes Research; and Clinical Practice, Year: 2011, vol. 93, No. 3, pp. 317-327.

Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.

Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.

Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.

Aenugu H.P.R et al. Near Infra Red Spectroscopy—An Overview, "International Journal of ChemTech Research" Year 2011, vol. 3, No. 2, pp. 825-836.

Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.

Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-port-steffens/download-16, the whole document.

Remington, The Science and Practice of Pharmacy, 22nd Edition, 2012, pp. 1-3.

Felix Kratz "A Clinical Update of Using Albumin as a Drug Vehicle—A Commentary" Journal of Controlled Release 2014 vol. 190 pp. 331-336.

* cited by examiner

SEQUENCE LISTING

<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 2
<211> LENGTH: 40
<212> TYPE: PRT
<213> ORGANISM: Heloderma suspectum

<400> SEQUENCE: 2

```
His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
        35                  40
```

SOLID COMPOSITIONS COMPRISING A GLP-1 AGONIST AND A SALT OF N-(8-(2-HYDROXYBENZOYL)AMINO)CAPRYLIC ACID

CROSS-REFERENCE TO RELATED APPLICATIONS

This application is a 35 U.S.C. §371 National Stage application of International Application PCT/EP2011/073060 (WO 2012/080471), filed Dec. 16, 2011, which claimed priority of European Patent Application 10195285.1, filed Dec. 16, 2010; this application claims priority under 35 U.S.C. §119 of U.S. Provisional Application 61/425,087; filed Dec. 20, 2010.

FIELD OF THE INVENTION

The present invention relates to solid compositions comprising a GLP-1 agonist and a salt of N-(8-(2-hydroxybenzoyl)amino)caprylic acid and their use in medicine.

BACKGROUND OF THE INVENTION

Human GLP-1 and analogues thereof have a low oral bioavailability. Exposure and bioavailability of human GLP-1 and analogues thereof is very low following oral administration. Human GLP-1 and analogues thereof can only be detected in plasma after oral administration if formulated with certain absorption enhancers in a specific amount. Steinert et al. (Am J Clin Nutr, October 2010; 92: 810-817) discloses oral administration of a tablet comprising GLP-1(7-36)amide and 150 mg sodium N-(8-(2-hydroxybenzoyl)amino)caprylate (SNAC). WO 2010/020978 discloses an oral pharmaceutical composition comprising a protein and N-(8-[2-hydroxybenzoyl)amino)caprylate (SNAC).

There is still a need for an optimized pharmaceutical composition for oral administration of a GLP-1 agonist such as a GLP-1 agonist comprising a substituent.

SUMMARY OF THE INVENTION

In some embodiments the invention relates to a solid composition for oral administration comprising a GLP-1 agonist and a salt of N-(8-(2-hydroxybenzoyl)amino)caprylic acid, wherein a) the amount of said salt of N-(8-(2-hydroxybenzoyl)amino)caprylic acid is at least 0.6 mmol or at least 0.8 mmol; and b) said GLP-1 agonist is GLP-1 (7-37), GLP-1(7-36)amide, exendin-4 or an analogue thereof, and wherein said GLP-1 agonist optionally comprises one substituent. In some embodiments the invention relates to the use of a composition as defined herein in medicine.

DESCRIPTION OF THE INVENTION

The present invention relates to solid compositions of a GLP-1 agonist and salt of N-(8-(2-hydroxybenzoyl)amino)caprylic acid. Surprisingly, the present inventors have found that solid compositions comprising certain amounts of a salt of N-(8-(2-hydroxybenzoyl)amino)caprylic acid, such as SNAC, are optimal for oral administration of GLP-1 agonists. Accordingly, the compositions provide improved exposure and/or bioavailability of the GLP-1 agonist.

Generally, the term "bioavailability" as used herein refers to the fraction of an administered dose of an active pharmaceutical ingredient (API), such as a GLP-1 agonist as defined herein, which reaches the systemic circulation unchanged. By definition, when an API is administered intravenously, its bioavailability is 100%. However, when it is administered via other routes (such as orally), its bioavailability decreases (due to incomplete absorption and first-pass metabolism). Knowledge about bioavailability is important when calculating dosages for non-intravenous routes of administration.

Absolute oral bioavailability is calculated as the relative exposure of the API in systemic circulation following oral administration (estimated as the area under the plasma concentration versus time curve, or AUC) compared to the exposure of the API following intravenous administration.

GLP-1 Agonist

The term "GLP-1 agonist" as used herein refers to a compound, which fully or partially activates the human GLP-1 receptor. In some embodiments the "GLP-1 agonist" binds to a GLP-1 receptor, e.g., with an affinity constant ($K_D$) or activate the receptor with a potency ($EC_{50}$) of below 1 µM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 agonist may be administered to an animal with increased blood glucose (e.g. obtained using an Intravenous Glucose Tolerance Test (IVGTT), a person skilled in the art will be able to determine a suitable glucose dosage and a suitable blood sampling regime, e.g. depending on the species of the animal, for the IVGTT) and the plasma insulin concentration measured over time.

In some embodiments the GLP-1 agonist is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 agonist, e.g., [Aib8] GLP-1(7-37) designates an analogue of GLP-1(7-37) wherein the naturally occurring Ala in position 8 has been substituted with Aib. In some embodiments the GLP-1 agonist comprises a maximum of twelve, such as a maximum of 10, 8 or 6, amino acids which have been alterered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID No: 1). In some embodiments the term "variant" refers to a compound which comprises one or more amino acid substitutions, deletions, additions and/or insertions.

In one embodiment the GLP-1 agonist exhibits at least 60%, 65%, 70%, 80% or 90% sequence identity to GLP-1(7-37) over the entire length of GLP-1(7-37). As an example of a method for determination of sequence identity between two analogues the two peptides [Aib8]GLP-1(7-37) and GLP-1(7-37) are aligned. The sequence identity of [Aib8]GLP-1(7-37) relative to GLP-1(7-37) is given by the number of aligned identical residues minus the number of different residues divided by the total number of residues in GLP-1(7-37). Accordingly, in said example the sequence identity is (31-1)/31.

In one embodiment the C-terminal of the GLP-1 agonist is an amide.

In some embodiments the GLP-1 agonist is GLP-1(7-37) or GLP-1(7-36)amide.

In some embodiments the GLP-1 agonist is exendin-4, the sequence of which is HGEGTFITSDLSKQMEEEAVR-LFIEWLKNGGPSSGAPPPS (SEQ ID No: 2).

In some embodiments the GLP-1 agonist comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid. In some embodiments the substituent comprises formula (X)

$$\text{HO} \overset{O}{\underset{}{\parallel}} \underset{n}{\overset{}{\phantom{|}}} \overset{O}{\underset{}{\parallel}} \quad (X)$$

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17. In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino) butyrylamino]ethoxy}ethoxy)acetylamino]ethoxy}ethoxy)acetyl].

In some embodiments the substituent is [2-(2-{2-[2-(2-{2-[(S)-4-carboxy-4-({trans-4-[(19-carboxynonadecanoylamino)methyl]cyclohexanecarbonyl}amino)butyrylamino]ethoxy}ethoxy)acetylamino]ethoxy}ethoxy)acetyl].

In some embodiments the GLP-1 agonist is semaglutide, also known as N-epsilon26-[2-(2-{2-[2-(2-{2-[(S)-4-carboxy-4-(17-carboxyheptadecanoylamino)butyrylamino]ethoxy}ethoxy)acetylamino]ethoxy}ethoxy)acetyl][Aib8,Arg34]GLP-1(7-37), which may be prepared as described in WO2006/097537, Example 4.

In some embodiments the composition comprises the GLP-1 agonist or a pharmaceutically acceptable salt, amide, or ester thereof. In some embodiments the composition comprises the GLP-1 agonist one or more pharmaceutically acceptable counter ions.

In some embodiments the dosage of GLP-1 is in the range of 0.01 mg to 100 mg. In some embodiments the composition comprises an amount of a GLP-1 agonist in the range of 0.1 to 40 mg or 1 to 20 mg. In some embodiments the composition comprises an amount of a GLP-1 agonist in the range of 5 to 20 mg, such as in the range of 5 to 15 mg, such as 5 mg, such as 10 mg, such as 15 mg, such as 20 mg.

In some embodiments the composition comprises an amount of a GLP-1 agonist in the range of 0.05 to 25 µmol, such as in the range of 0.5 to 2.5 µmol.

In some embodiments the GLP-1 agonist is selected from one or more of the GLP-1 agonists mentioned in WO93/19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 agonist is selected from the group consisting of N-epsilon37{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy]ethoxy}acetyl [desaminoHis7,Glu22,Arg26,Arg34,Lys37]GLP-1(7-37)amide; N-epsilon26{2-[2-(2-{2-[2-((R)-3-carboxy-3-{[1-(19-carboxynonadecanoyl)piperidine-4-carbonyl]amino}propionylamino)ethoxy]ethoxy}acetylamino)ethoxy] ethoxy}acetyl [desaminoHis7, Arg34] GLP-1-(7-37); N-epsilon37{2-[2-(2-{2-[2-((S)-3-carboxy-3-{[1-(19-carboxy-nonadecanoyl) piperidine-4-carbonyl]amino}propionylamino)ethoxy] ethoxy}acetylamino)ethoxy]ethoxy}acetyl[Aib8,Glu22, Arg26,Arg34,Lys37]GLP-1-(7-37)amide; N-epsilon37-[2-(2-[2-(2-[2-(2-((R)-3-[1-(17-carboxyheptadecanoyl) piperidin-4-ylcarbonylamino]3-carboxypropionylamino) ethoxy)ethoxy]acetylamino)ethoxy]ethoxy)acetyl][, DesaminoHis7, Glu22 Arg26, Arg34, Phe(m-CF3)28]GLP-1-(7-37)amide; N-epsilon26-[(S)-4-carboxy-4-({trans-4-[(19-carboxynonadecanoylamino)methyl]cyclo-hexanecarbonyl}amino)butyryl][Aib8,Arg34]GLP-1-(7-37); N-epsilon26-{4-[(S)-4-carboxy-4-({trans-4-[(19-carboxynonadecanoylamino)methyl] cyclohexanecarbonyl}amino)butyrylamino]butyryl}[Aib8, Arg34]GLP-1-(7-37); N-epsilon26-[2-(2-{2-[(S)-4-carboxy-4-({trans-4-[(19-carboxy-nonadecanoylamino) methyl]cyclohexanecarbonyl}amino)butyrylamino] ethoxy}ethoxy)acetyl][Aib8,Arg34]GLP-1-(7-37)amide; N-epsilon26-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy) acetyl][Aib8,Arg34]GLP-1-(7-37)amide; N-epsilon37-[2-(2-{2-[2-(2-{2-[(S)-4-carboxy-4-({trans-4-[(19-carboxy-nonadecanoylamino) methyl]cyclohexanecarbonyl}amino)butyrylamino] ethoxy}ethoxy)acetylamino]ethoxy}ethoxy)acetyl][Aib8, Glu22,Arg26, Arg34,Lys37]GLP-1-(7-37)amide; N-epsilon37-[2-(2-{2-[2- (2-{2-[(S)-4-carboxy-4-({trans-4-[(19-carboxy-nonadecanoylamino)methyl] cyclohexanecarbonyl}amino) butyrylamino]ethoxy}ethoxy) acetylamino]ethoxy]ethoxy)acetyl][DesaminoHis7,Glu22, Arg26,Arg34,Lys37]GLP-1-(7-37)amide; N-epsilon37-[2-(2-{2-[2-(2-{2-[(S)-4-carboxy-4-({4-[(trans-19-carboxy-nonadecanoylamino)methyl]cyclohexanecarbonyl}amino) butyrylamino]ethoxy}ethoxy)acetylamino]ethoxy}ethoxy) acetyl][DesaminoHis7, Arg26,Arg34,Lys 37]GLP-1-(7-37) amide; N-epsilon37-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy)acetyl][DesaminoHis7,Glu22, Arg26, Arg34,Lys37]GLP-1-(7-37); N-epsilon26[2-(2-{2-[2-(2-{2-[(S)-4-carboxy-4-({4-[(19-carboxy-nonadecanoylamino)methyl]cyclohexanecarbonyl}amino)

butyrylamino]ethoxy}ethoxy)acetylamino]ethoxy}ethoxy) acetyl[Aib8, Lys 26]GLP-1 (7-37)amide; N-epsilon26 [2-(2-[2-(2-[2-(2-((S)-2-[trans-4-((9-carboxynonadecanoylamino] methyl) cyclohexylcarbonylamino]-4-carboxybutanoylamino)ethoxy)ethoxy]acetylamino) ethoxy]ethoxy)acetyl][Aib8, Lys26]GLP-1 (7-37)amide; N-epsilon37-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy)acetyl][DesaminoHis7, Arg26, Arg34,Lys37]GLP-1-(7-37); N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino] ethoxy}ethoxy)acetylamino]ethoxy}ethoxy)acetyl] [DesaminoHis7,G lu22,Arg26,Glu30,Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino}butyrylamino]ethoxy}ethoxy) acetyl][Aib8,Arg34]GLP-1-(7-37); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino] dodecanoylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoyl-sulfamoyl)butyrylamino]hexanoylamino}butyrylamino)butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{4-[4-(16-(1H-tetrazol-5-yl)hexadecanoylsulfamoyl)butyrylamino]butyrylamino}butyrylamino)butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]-dodecanoylamino}butyrylamino) butyrylamino]ethoxy}ethoxy)acetyl][Aib8,Arg34]GLP-1-(7-34); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino) butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoyl sulfamoyl) butyrylamino]dodecanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl) hexadecanoylsulfamoyl)butyrylamino]hexanoylamino] butyrylamino)butyrylamino]ethoxy}ethoxy)acetyl][Aib8, Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino] hexanoylamino}butyrylamino)butyrylamino] ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino) butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino]butyryl-amino)butyrylamino] ethoxy}ethoxy)acetyl][Aib8,Lys33,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino)butyrylamino] ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[2-(2-{2-[(S) -4-carboxy-4-((S)-4-carboxy-4-{12-[4-(16-(1H -tetrazol-5-yl)hexadecanoylsulfamoyl) butyrylamino] dodecanoylamino}butyrylamino)butyrylamino] ethoxy}ethoxy) acetylamino]ethoxy}ethoxy)acetylamino] ethoxy}ethoxy)acetylamino]ethoxy}ethoxy)acetylamino] ethoxy}ethoxy)acetylamino]ethoxy}ethoxy)acetyl][Aib8, Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino] dodecanoylamino}butyrylamino) butyrylamino] ethoxy}ethoxy)acetyl][Aib8, Glu22, Arg26, Arg34, Lys37] GLP-1-(7-37)amide; N-epsilon37-[2-(2-{2-[(S)-4-carboxy-4-((S)-4-carboxy-4-{12-[4-(16-(1H-tetrazol-5-yl) hexadecanoylsulfamoyl)butyrylamino] dodecanoylamino}butyrylamino)butyrylamino] ethoxy}ethoxy)acetyl][DesaminoHis7, Glu22, Arg26, Arg34, Lys37]GLP-1-(7-37)amide; N -epsilon37{2-[2-(2-{2-[2-((R)-3-carboxy-3-{[1-(19-carboxy-nonadecanoyl)piperidine-4-carbonyl]amino}propionylamino)ethoxy] ethoxy]acetylamino)ethoxy]ethoxy}acetyl [desaminoHis7, Glu22, Arg26, Arg34,Lys37]GLP-1(7-37)amide; N-epsilon37{2-[2-(2-{2-[2-((S)-3-carboxy-3-{[1-(19-carboxynonadecanoyl)piperidine-4-carbonyl] amino}propionylamino) ethoxy]ethoxy}acetylamino) ethoxy]ethoxy}acetyl [Aib8,Glu22, Arg26, Arg34, Lys37] GLP-1-(7-37)amide; N-epsilon37-[2-(2-[2-(2-[2-((R)-3-[1-(17-carboxyhepta-decanoyl)piperidin-4-ylcarbonylamino]3-carboxy propionylamino)ethoxy) ethoxy]acetylamino)ethoxy]acetyl][DesaminoHis7, Glu22, Arg26, Arg34, Phe(m-CF3)28]GLP-1-(7-37)amide; N-epsilon37-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy)acetyl][Aib8, Glu22, Arg26, Arg34, Lys37]GLP-1-(7-37)amide; N-epsilon37-[2-(2-{2-[2-(2-{2-[(S)-4-carboxy-4-({trans-4-[(19-carboxy-nonadecanoylamino)methyl]cyclohexanecarbonyl}amino)butyrylamino]ethoxy}ethoxy) acetylamino]ethoxy}ethoxy)acetyl] [DesaminoHis7,Glu22,Arg26,Arg34,Lys37]GLP-1-(7-37) amide; N-epsilon37-[2-(2-{2-[2-(2-{2-[(S)-4-carboxy-4-({trans-4-[(19-carboxy-nonadecanoylamino) methyl] cyclohexanecarbonyl}amino)butyrylamino]ethoxy}ethoxy) acetylamino]ethoxy}ethoxy)acetyl][DesaminoHis7,Glu22, Arg26,Arg34, Lys37]GLP-1-(7-37); N-epsilon37-[2-(2-{2-[2-(2-{2-[(S)-4-carboxy-4-({trans-4-[(19-carboxy-nonadecanoylamino) methyl]cyclohexanecarbonyl}amino) butyrylamino]ethoxy}ethoxy)acetylamino]ethoxy}ethoxy) acetyl][DesaminoHis7,Glu22,Arg26,Glu30,Arg34, Lys37] GLP-1-(7-37); N-epsilon37-[2-(2-{2-[(S) -4-carboxy-4-((S)-4-carboxy-4-{12-[4-(16-(1H-tetrazol-5-yl) hexadecanoyl-sulfamoyl) butyrylamino] dodecanoylamino}butyrylamino)butyrylamino] ethoxy}ethoxy)acetyl][Aib8,Glu22,Arg26,Arg34,Lys37] GLP-1-(7-37)amide; N-epsilon37-[2-(2-{2-[(S)-4-carboxy-4-((S)-4-carboxy-4-{12-[4-(16-(1H-tetrazol-5-yl) hexadecanoylsulfamoyl)butyrylamino] dodecanoylamino}butyrylamino)butyrylamino] ethoxy}ethoxy)acetyl][DesaminoHis7,Glu22,Arg26,Arg34, Lys37]GLP-1-(7-37)amide; N-epsilon37-(3-((2-(2-(2-(2-(2-Hexadecyloxyethoxy)ethoxy)ethoxy)ethoxy)ethoxy)) propionyl)[DesaminoHis7,Glu22,Arg26,Arg34,Lys37] GLP-1(7-37)-amide; N-epsilon37-{2-(2-(2-(2-[2-(2-(4-(hexadecanoylamino)-4-carboxybutyryl-amino)ethoxy) ethoxy]ethoxy)ethoxy)acetyl)}-desaminoHis7, Glu22,Arg26, Glu30,Arg34,Lys37]GLP-1-(7-37)amide; N-epsilon37-{2-(2-(2-(2-[2-(2-(4-(hexadecanoylamino)-4-carboxy-butyryl-amino) ethoxy)ethoxy]acetyl)ethoxy) ethoxy)acetyl)}-desaminoHis7,Glu22, Arg26, Arg34,Lys37

GLP-1-(7-37)amide; N-epsilon37-(2-(2-(2-(2-(2-(2-(2-(2-(2-(octadecanoyl-amino)ethoxy)ethoxy)acetylamino) ethoxy) ethoxy)acetylamino) ethoxy)ethoxy)acetyl) [desaminoHis7,Glu22,Arg26,Arg34,Lys37]GLP-1(7-37) amide; N-epsilon37-[4-(16-(1H-Tetrazol-5-yl) hexadecanoylsulfamoyl)butyryl] [Desamino-His7,Glu22, Arg26, Arg34, Lys37]GLP-1-(7-37)amide; N-epsilon37-[2-(2-[2-[2-(2-[(S)-4-carboxy-4-(19-carboxynonadecanoylamino)butyrylamino]ethoxy}ethoxy) acetylamino]ethoxy}ethoxy)acetyl][DesaminoHis7,Glu22, Arg26, Arg34,Lys37]GLP-1-(7-37); N-epsilon37-(2-{2-[2-((S)-4-carboxy-4-{(S)-4-carboxy-4-[(S)-4-carboxy-4-(19-carboxy-nonadecanoylamino)butyrylamino] butyrylamino}butyrylamino)ethoxy]ethoxy}acetyl) [DesaminoHis7,Glu22,Arg26,Arg34,Lys37]GLP-1-(7-37); N-epsilon37-{2-[2-(2-{(S)-4-[(S)-4-(12-{4-[16-(2-tert-Butyl-2H-tetrazol-5-yl)-hexadecanoylsulfamoyl] butyrylamino}dodecanoylamino)-4-carboxybutyrylamino]-4-carboxybutyrylamino}ethoxy)ethoxy]acetyl} [DesaminoHis7,Glu22,Arg26,Arg34,Lys37]GLP-1(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][Aib8,Glu22, Arg26,Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][Aib8,Glu22,Arg26,Arg34,epsilon-Lys37] GLP-1-(7-37)peptide; N -epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl][desaminoHis7, Glu22,Arg26,Arg34,Lys37] GLP-1-(7-37); N-epsilon36-[2-(2-{2-[2-(2-{2-[(S)-4-carboxy-4-(15-carboxy-pentadecanoylamino)-butyrylamino]-ethoxy}-ethoxy) -acetylamino]-ethoxy}-ethoxy)-acetyl][desaminoHis7, Glu22,Arg26,Glu30,Arg34, Lys36]GLP-1(7-37)-Glu-Lys peptide; N-epsilon37-[2-(2-{2-[2-(2-{2-[(S)-4-carboxy-4-({trans-4-[(19-carboxynonadecanoylamino)methyl] cyclohexanecarbonyl}amino)butyryl-amino] ethoxy}ethoxy)acetylamino]ethoxy}ethoxy)acetyl][Aib8, Glu22,Arg26,Arg34,Lys37]GL P-1-(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy) -acetyl]-[Aib8,Glu22, Arg26, Arg34,Aib35,Lys37]GLP-1-(7-37); N-epsilon37-[(S)-4-carboxy-4-(2-{2-[2-{2-[2-(17-carboxyheptadecanoylamino)ethoxy]ethoxy}acetylamino) ethoxy]ethoxy}acetylamino)butyryl][Aib8,Glu22,Arg26, 34,Lys37]GLP-1(7-37); N-epsilon37-[2-(2-[2-[2-(2-[2-(2-[4-(17-carboxyheptadecanoylamino)-4(S) -carboxybutyrylamino]ethoxy)ethoxy]acetylamino]ethoxy]ethoxy)acetyl] [ImPr7,Glu22, Arg26,34,Lys37], GLP-1-(7-37); N-epsilon26-{2-[2-(2-{2-[2-(2-{(S)-4-carboxy-4-[10-(4-carboxyphenoxy) decanoylamino]butyrylamino}ethoxy) ethoxy]acetylamino}ethoxy) ethoxy]acetyl}, N-epsilon37-{2-[2-(2-{2-[2-(2-{(S)-4-carboxy-4-[10-(4-carboxyphenoxy) decanoylamino]butyrylamino}ethoxy)ethoxy] acetylamino}ethoxy)ethoxy]acetyl]-[Aib8,Arg34,Lys37] GLP-1(7-37)-OH; N-epsilon26 (17-carboxyheptadecanoyl) -[Aib8,Arg34]GLP-1-(7-37)-peptide; N-epsilon26-(19-carboxynonadecanoyl) -[Aib8,Arg34]GLP-1-(7-37); N-epsilon26-(4-{[N-(2-carboxyethyl)-N-(15-carboxypentadecanoyl)amino]methyl}benzoyl[Arg34]GLP-1(7-37); N-epsilon26-[2-(2-[2-[2-(2-[2-(2-[4-(17-carboxyheptadecanoylamino)-4(S)-carboxybutyrylamino]ethoxy)ethoxy] acetylamino]ethoxy)ethoxy]acetyl][Aib8,Arg34]GLP-1-(7-37); N-epsilon26-[2-(2-[2-(2-[2-(2-[4-(19-carboxynonadecanoylamino)-4(S)-carboxybutyrylamino] ethoxy)ethoxy]acetylamino)ethoxy]ethoxy)acetyl][Aib8, Arg34]GLP-1-(7-37); N-epsilon26-[2-(2-[2-(2-[2-(2-[4-(17-carboxyheptadecanoylamino)-4(S)-carboxybutyrylamino] ethoxy)ethoxy]acetylamino)ethoxy]ethoxy)acetyl][3-(4-Imidazolyl)Propionyl7,Arg34]GLP-1-(7-37); N-epsilon26-[2-(2-[2-(2-[2-(2-[4-(17-carboxyheptadecanoylamino)-(carboxymethylamino)acetylamino]ethoxy)ethoxy] acetylamino)ethoxy]ethoxy)acetyl][Aib8,Arg34]GLP-1-(7-37); N-epsilon26-[2-(2-[2-(2-[2-(2-[4-(17-carboxyheptadecanoylamino)-3(S)-Sulfopropionylamino] ethoxy)ethoxy]acetylamino)ethoxy]ethoxy)acetyl][Aib8, Arg34]GLP-1-(7-37); N-epsilon26-[2-(2-[2-(2-[2-(2-[4-(17-carboxyheptadecanoylamino)-4(S)-carboxybutyrylamino] ethoxy)ethoxy]acetylamino)ethoxy]ethoxy)acetyl][Gly8, Arg34] GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Aib8,Arg34]GLP-1-(7-37)-amide; N-epsilon26-[2-(2-[2-(2-[2-(2-[4-(17-carboxyheptadecanoylamino)-4(S)-carboxybutyrylamino]ethoxy)ethoxy] acetylamino)ethoxy]ethoxy)acetyl][Aib8,Arg34,Pro37] GLP-1-(7-37)amide; Aib8,Lys26(N-epsilon26-{2-(2-(2-(2-[2-(2-(4-(pentadecanoylamino)-4-carboxybutyrylamino) ethoxy)ethoxy]acetyl)ethoxy) ethoxy)acetyl)}), Arg34) GLP-1H(7-37)-OH; N-epsilon26-[2-(2-[2-(2-[2-(2-[4-{[N-(2-carboxyethyl)-N-(17-carboxyheptadecanoyl)amino] methyl}benzoyl)amino]ethoxy)ethoxy]acetylamino)ethoxy) ethoxy)acetyl][Aib8,Arg34]GLP-1(7-37); N-alpha7-formyl, N-epsilon26-[2-(2-[2-(2-[2-(2-[4-(17-carboxyheptadecanoyl-amino)-4(S)-carboxybutyrylamino]ethoxy)ethoxy] acetylamino)ethoxy]ethoxy)acetyl][Arg34]GLP-1-(7-37); N-epsilon2626-[2-(2-[2-(2-[2-(2-[4-(17-carboxyheptadecanoylamino)-4(S)-carboxybutyrylamino]ethoxy)ethoxy] acetylamino)ethoxy]ethoxy)acetyl][Aib8, Glu22, Arg34] GLP-1-(7-37); N-epsilon26{3-[2-(2-{2-[2-(2-{2-[2-(2-[4-(15-(N—((S)-1,3-dicarboxypropyl)carbamoyl) pentadecanoylamino)-(S)-4-carboxybutyrylamino]ethoxy) ethoxy]ethoxy}ethoxy]ethoxy}ethoxy]ethoxy] propionyl][Aib8,Arg34]GLP -1-(7-37); N-epsilon26-[2-(2-[2-(2-[2-(2-[4-{[N-(2-carboxyethyl)-N-(17-carboxyheptadecanoyl)amino]methyl}benzoyl)amino](4 (S)-carboxybutyryl-amino)ethoxy)ethoxy]acetylamino) ethoxy]ethoxy)acetyl][Aib8,Arg34]GLP-1(7-37); N-epsilon26-{(S)-4-carboxy-4-((S)-4-carboxy-4-((S)-4-carboxy-4-((S)-4-carboxy-4-(19-carboxy -nonadecanoylamino)butyrylamino)butyrylamino)butyrylamino)butyrylamino}[Aib8,Arg34]GLP-1(7-37); N-epsilon26-4-(17-carboxyheptadecanoyl-amino)-4(S) -carboxybutyryl-[Aib8, Arg34]GLP-1-(7-37); N-epsilon26-{3-[2-(2-{2-[2-(2-{2-[2-[4-(17-carboxyheptadecanoylamino)-4(S)-carboxybutyrylamino]ethoxy)ethoxy]ethoxy}ethoxy) ethoxy]ethoxy}ethoxy]propionyl}[Aib8,Arg34] GLP-1-(7-37); N-epsilon26-{2-(2-(2-(2-[2-(2-(4-(17-carboxyheptadecanoylamino)-4-carboxybutyrylamino) ethoxy)ethoxy]acetyl)ethoxy)ethoxy)acetyl)}-[Aib8,22,27, 30,35,Arg34,Pro37, Lys26]GLP-1(7-37)amide; N-epsilon26-[2-(2-[2-[4-(21-carboxyuneicosanoylamino)-4(S) -carboxybutyrylamino]ethoxy]ethoxy)acetyl][Aib8,Arg34] GLP-1-(7-37); and N-epsilon26-[2-(2-[2-(2-[2-(2-[4-(21-carboxyuneicosanoylamino)-4(S)-carboxybutyrylamino] ethoxy)ethoxy]acetylamino)ethoxy]ethoxy)acetyl][Aib8, Arg34]GLP-1-(7-37).

Delivery Agent: Salt of N-(8-(2-hydroxybenzoyl)amino)caprylic acid

The delivery agent used in the present invention is a salt of N-(8-(2-hydroxybenzoyl)amino)caprylic acid. The structural formula of N-(8-(2-hydroxybenzoyl)amino)caprylate is shown in formula (I).

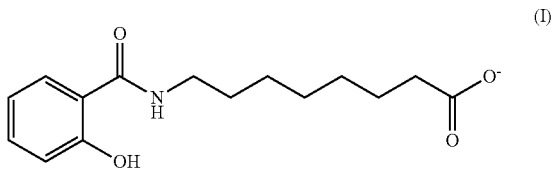 [SMILES: O=C([O-])CCCCCCCNC(=O)c1ccccc1O]

In some embodiments the salt of N-(8-(2-hydroxybenzoyl) amino)caprylic acid comprises one monovalent cation, two monovalent cations or one divalent cation. In some embodiments the salt of N-(8-(2-hydroxybenzoyl)amino)caprylic acid is selected from the group consisting of the sodium salt, potassium salt and calcium salt of N-(8-(2-hydroxybenzoyl) amino)caprylic acid.

Salts of N-(8-(2-hydroxybenzoyl)amino)caprylate may be prepared using the method described in e.g. WO96/030036, WO00/046182, WO01/092206 or WO2008/028859.

The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino)caprylic acid as well as combinations thereof. In some embodiments the delivery agent is a salt of N-(8-(2-hydroxybenzoyl)amino)caprylic acid as described in WO2007/121318.

In some embodiments the delivery agent is sodium N-(8-(2-hydroxybenzoyl)amino)caprylate (referred to as "SNAC" herein), also known as sodium 8-(salicyloylamino)octanoate.

In some embodiments the amount of the salt of N-(8-(2-hydroxybenzoyl) amino) caprylic acid in the composition is at least 0.6 mmol, such as selected from the group consisting of at least 0.65 mmol, at least 0.7 mmol, at least 0.75 mmol, at least 0.8 mmol, at least 0.8 mmol, at least 0.9 mmol, at least 0.95 mmol and at least 1 mmol. In some embodiments the amount of the salt of N-(8-(2-hydroxybenzoyl)amino)caprylic acid in the composition is in the range of 0.6-2.1 mmol or 0.6-1.9 mmol. In some embodiments the amount of the salt of N-(8-(2-hydroxybenzoyl) amino)caprylic acid in the composition is in the range of 0.7-1.7 mmol or 0.8-1.3 mmol. In some embodiments the amount of the salt of N-(8-(2-hydroxybenzoyl)amino)caprylic acid in the composition is up to 2.1 mmol, such as selected from the group consisting of up to 2.1 mmol, up to 2 mmol, up to 1.9 mmol, up to 1.8 mmol, up to 1.7 mmol, up to 1.6 mmol, up to 1.5 mmol, up to 1.4 mmol, up to 1.3 mmol, up to 1.2 mmol and up to 1.1 mmol. In some embodiments the amount of the salt of N-(8-(2-hydroxybenzoyl)amino)caprylic acid is 1 mmol, such as 1.08 mmol.

In some embodiments the amount of SNAC in the composition is at least 175 mg, such as an amount selected from the group consisting of at least 200 mg, at least 210 mg, at least 220 mg, at least 230 mg, at least 240 mg, at least 250 mg, at least 260 mg, at least 270 mg and at least 280 mg. In some embodiments the amount of SNAC in the composition is in the range of 175-575 mg, such as 200-500 mg or 250-400 mg. In some embodiments the amount of SNAC in the composition is up to 575 mg, such as an amount selected from the group consisting of up to 550 mg, up to 525 mg, up to 500 mg, up to 475 mg, up to 450 mg, up to 425 mg, up to 400 mg, up to 375 mg, up to 350 mg and up to 325 mg. In some embodiments the amount of SNAC in the composition is 300 mg.

In some embodiments the molar ratio between GLP-1 agonist and delivery agent in the composition is less than 10, such as less than 5 or less than 1.

Composition

The composition of the present invention is a solid composition and is administered by the oral route.

In some embodiments the composition comprises at least one pharmaceutically acceptable excipient. The term "excipient" as used herein broadly refers to any component other than the active therapeutic ingredient(s). The excipient may be an inert substance, an inactive substance, and/or a not medicinally active substance. The excipient may serve various purposes, e.g. as a carrier, vehicle, filler, binder, lubricant, glidant, disintegrant, flow control agents, crystallization retarders, solubilizers, stabilizer, colouring agent, flavouring agent, surfactant, emulsifier and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005). In some embodiments the excipients may be selected from binders, such as polyvinyl pyrrolidone (povidone), etc.; fillers such as cellulose powder, microcrystalline cellulose, cellulose derivatives like hydroxymethylcellulose, hydroxyethylcellulose, hydroxypropylcellulose and hydroxy-propylmethylcellulose, dibasic calcium phosphate, corn starch, pregelatinized starch, etc.; lubricants and/or glidants such as stearic acid, magnesium stearate, sodium stearylfumarate, glycerol tribehenate, etc.; flow control agents such as colloidal silica, talc, etc.; crystallization retarders such as Povidone, etc.; solubilizers such as Pluronic, Povidone, etc.; colouring agents, including dyes and pigments such as Iron Oxide Red or Yellow, titanium dioxide, talc, etc.; pH control agents such as citric acid, tartaric acid, fumaric acid, sodium citrate, dibasic calcium phosphate, dibasic sodium phosphate, etc.; surfactants and emulsifiers such as Pluronic, polyethylene glycols, sodium carboxymethyl cellulose, polyethoxylated and hydrogenated castor oil, etc.; and mixtures of two or more of these excipients and/or adjuvants.

In some embodiments the composition comprises at least 60% (w/w) delivery agent, less than 10% (w/w) binder, 5-40% (w/w) filler, and less than 10% (w/w) lubricant or glidant.

In some embodiments the composition comprises at least 60% (w/w), such as at least 70% (w/w) or at least 75% (w/w), delivery agent.

In some embodiments the composition comprises 0.1-10% (w/w), such as 0.2-4% (w/w) or 0.5-3% (w/w), of binder. In some embodiments the composition comprises 1% (w/w) or 2% (w/w) of binder. The composition may comprise a binder, such as povidone; starches; celluloses and derivatives thereof, such as microcrystalline cellulose, e.g., AVICEL PH from FMC (Philadelphia, PA), hydroxypropyl cellulose hydroxylethyl cellulose and hydroxylpropylmethyl cellulose METHOCEL from Dow Chemical Corp. (Midland, Mich.); sucrose; dextrose; corn syrup; polysaccharides; and gelatin.

The binder may be selected from the group consisting of dry binders and/or wet granulation binders. Suitable dry binders are, e.g., cellulose powder and microcrystalline cellulose, such as Avicel PH 102 and Avicel PH 200. In some embodiments the composition comprises avicel, such as avicel PH 102. Suitable binders for wet granulation or dry granulation are corn starch, polyvinyl pyrrolidone (povidon), vinylpyrrolidone-vinylacetate copolymer (copovidone) and cellulose derivatives like hydroxymethylcellulose, hydroxyethylcellulose, hydroxypropylcellulose and hydroxyl-propylmethylcellulose. In some embodiments the composition comprises povidone.

In some embodiments the composition comprises 5-40% (w/w), such as 10-30% (w/w) or 5-25% (w/w), of filler. In some embodiments the composition comprises 10.9% (w/w) or 18%(w/w) of filler, or comprises 19.5% (w/w) or 20.5 (w/w) of filler. The filler may be selected from lactose, mannitol, erythritol, sucrose, sorbitol, calcium phosphate, such as calciumhydrogen phosphate, microcrystalline cellulose, powdered cellulose, confectioner's sugar, compressible sugar, dextrates, dextrin and dextrose. In some embodiments the composition comprises microcrystalline cellulose, such as Avicel PH 102 or Avicel PH 200.

In some embodiments the composition comprises 0.1-10% (w/w) or 0.5-5% (w/w), such as 1-3.5% (w/w) or 1% (w/w), of lubricant and/or a glidant. In some embodiments the composition comprises a lubricant and/or a glidant, such as talc, magnesium stearate, calcium stearate, zinc stearate, glyceryl behenate, polyethylene oxide polymers, sodium lauryl sulfate, magnesium lauryl sulfate, sodium oleate, sodium stearyl fumarate, stearic acid, hydrogenated vegetable oils, silicon dioxide and/or polyethylene glycol. In some embodiments the composition comprises magnesium stearate.

In some embodiments the composition comprises a disintegrant, such as sodium starch glycolate, polacrilin potassium, sodium starch glycolate, crospovidon, croscarmellose, sodium carboxymethylcellulose or dried corn starch.

The composition may comprise one or more surfactants, for example a surfactant, at least one surfactant, or two different surfactants. The term "surfactant" refers to any molecules or ions that are comprised of a water-soluble (hydrophilic) part, and a fatsoluble (lipophilic) part. The surfactant may e.g. be selected from the group consisting of anionic surfactants, cationic surfactants, nonionic surfactants, and/or zwitterionic surfactants.

Still further, the composition may be formulated as is known in the art of oral formulations of insulinotropic compounds, e.g. using any one or more of the formulations described in WO 2008/145728.

A composition may also be used in the formulation of site specific, controlled, sustained, protracted, prolonged, delayed, pulsatile, retarded, and/or slow release drug delivery systems.

The composition of the invention may be prepared as is known in the art.

The composition may be administered in several dosage forms, for example as a tablet; a coated tablet; a chewing gum; a capsule such as hard or soft gelatine capsules or a powder. The composition may further be compounded in a drug carrier or drug delivery system, e.g. in order to improve stability and/or solubility or further improve bioavailability. The composition may be a freeze-dried or spray-dried composition.

The composition may be in the form of a tablet. In some embodiments the weight of the tablet is in the range of 175 mg to 1000 mg, such as in the range of 175-250 mg, 300-500 mg or 500-900 mg, or such as about 200 mg, about 400 mg or about 700 mg. In some embodiments the weight of the tablet is in the range of 200 mg to 1000 mg, such as in the range of 500-700 mg or 600-1000 mg, or such as about 200 mg, about 400 mg, about 600 mg or about 800 mg.

In some embodiments the composition may be granulated prior to being compacted. The composition may comprise an intragranular part and an extragranular part, wherein the intragranular part has been granulated and the extragranular part has been added after granulation. The intragranular part may comprise the GLP-1 agonist, the delivery agent and a binder. In some embodiments the intragranular part comprises povidone. The extragranular part may comprise a filler, a lubricant and/or a glidant. In some embodiments the extragranular part comprises microcrystalline cellulose, such as avicel, e.g. avicel PH120 or avicel PH200. In some embodiments the extragranular part comprises magnesium stearate.

To prepare a dry blend of tabletting material, the various components are weighed, optionally delumped and then combined. The mixing of the components may be carried out until a homogeneous blend is obtained.

If granules are to be used in the tabletting material, granules may be produced in a manner known to a person skilled in the art, for example using wet granulation methods known for the production of "built-up" granules or "broken-down" granules. Methods for the formation of built-up granules may operate continuously and comprise, for example simultaneously spraying the granulation mass with granulation solution and drying, for example in a drum granulator, in pan granulators, on disc granulators, in a fluidized bed, by spray-drying or spray-solidifying, or operate discontinuously, for example in a fluidized bed, in a rotary fluid bed, in a batch mixer, such as a high shear mixer or a low shear mixer, or in a spray-drying drum. Methods for the production of broken-down granules, which may be carried out discontinuously and in which the granulation mass first forms a wet aggregate with the granulation solution, which is subsequently comminuted or by other means formed into granules of the desired size and the granules may then be dried. Suitable equipment for the granulation step are planetary mixers, low shear mixers, high shear mixers, extruders and spheronizers, such as an apparatus from the companies Loedige, Glatt, Diosna, Fielder, Collette, Aeschbach, Alexanderwerk, Ytron, Wyss & Probst, Werner & Pfleiderer, HKD, Loser, Fuji, Nica, Caleva and Gabler. Granules may be also formed by dry granulation techniques in which the pharmaceutically active agent is compressed with the excipients to form relatively large moldings, for example slugs or ribbons, which are comminuted by grinding, and the ground material serves as the tabletting material to be later compacted. Suitable equipment for dry granulation is roller compaction equipment from Gerteis, such as Gerteis MINI-PACTOR.

To compact the tabletting material into a solid oral dosage form, for example a tablet, a tablet press may be used. In a tabletting press, the tabletting material is filled (e.g. force fed or gravity fed) into a die cavity. The tabletting material is then compacted by a punch with pressure. Subsequently, the resulting compact, or tablet is ejected from the tabletting press. The above mentioned compaction process is subsequently referred to herein as the "compaction process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom).

In some embodiments the method of preparation of the tablet comprises a) wet granulation of a mixture comprising the GLP-1 agonist, the delivery agent and a binder; b) optionally drying the wet granulate; c) blending of the dried wet granulates with at least a filler and at least a lubricant or a glidant, and then d) compression of the blend into tablets. The granulation may be a wet granulation or a dry granulation.

Disintegration time: In some embodiments the disintegration time of the tablet is in the range of 7 minutes to 15 minutes, such as in the range of 8 minutes to 13 minutes. Disintegration time may be determined using a Pharma Test PTZ AUTO disintegration test apparatus. The disintegration apparatus consists of a basket rack holding 2×6 plastic tubes, open at the top and bottom, the bottom of the tube is covered by a screen. Tablets are placed in the tubes and on top of the tablets are placed discs for automated disintegration detection. The basket is immersed in 800 ml purified water maintained at 37° C., in a 1L beaker. Time for complete disintegration is measured. Furthermore, tablets may be observed visually for surface eroding behaviour during the disintegration test.

In some embodiments the tablet of the invention co-releases the active ingredients and the delivery agent by surface erosion; hence, the tablets becomes smaller and smaller with time by dissolution primarily from the surface from non-disintegrated tablets. Concurrent release: In some embodiments the compositions show concurrent release of the GLP-1 agonist and the delivery agent from the surface of the tablet. This can be tested by visual inspection during the disintegration test; the tablets do not have concurrent release of the GLP-1 agonist and the delivery agent from the surface of the tablet if the tablet breaks into smaller parts during the first 8 minutes of the disintegration test.

Dissolution test: Another test for concurrent release of the GLP-1 agonist and the delivery agent is the dissolution test. Here, the rate of appearance (in percentage) of the GLP-1 agonist and the delivery agent is measured. The dissolution test may be carried out as described in the following: Dissolution is performed on a Varian 705 DS. The analysis is based on the pharmacopeia method Ph Eur 2.9.3, Apparatus 2 (Paddle apparatus). 100 ml mini vessel with mini-paddles is used, and paddle speed is 75 rpm. After 120 minutes, the paddle speed is changed to 250 rpm. The dissolution medium used for the dissolution test is 100 ml of 200 mM KH2PO4 (containing 0.07% Tween 80 to avoid the GLP-1 agonist from sticking to the wall of the bath and to the paddle), with pH 6.8. Samples are taken after 5, 15, 30, 45, 60, 120 and 135 minutes. The volume of the sample is 2 ml, and the sample is taken with a disposable syringe. After each sample is taken, the same volume (2 ml) of the dissolution medium is added to the bath, in order to keep the total volume of 100 ml constant. The sample is pressed through a 0.22 µm Millex®-GV filter. Finally, the samples are analysed for concentration of the GLP-1 agonist and for concentration of the delivery agent by UPLC.

Hardness test: The hardness of the tablets is measured with a Pharma Test (33AA02), which measures the force required to disrupt the tablet, and the test is based on the pharmacopeia method Ph Eur 2.9.8.

The treatment with a composition according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, R×R agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, R×R (retinoid×receptor) modulators, TR β agonists; histamine H3 antagonists, Gastric Inhibitory Polypeptide agonists or antagonists (GIP analogs), gastrin and gastrin analogs.

Additional embodiments of the compositions of the invention are described in the section headed "particular embodiments" before the experimental section.

Pharmaceutical Indications

The present invention also relates to a composition of the invention for use as a medicament. In particular embodiments the composition of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix). In another particular embodiment, the indication is (i). In a further particular embodiment the indication is (v). In a still further particular embodiment the indication is (iix). In some embodiments the indications are type 2 diabetes and/or obesity.

Further Embodiments

1. A solid composition for oral administration comprising a GLP-1 agonist and a salt of N-(8-(2-hydroxybenzoyl)amino)caprylic acid, wherein the amount of said salt of N-(8-(2-hydroxybenzoyl)amino)caprylic acid is at least 0.6 mmol.
2. A solid composition for oral administration comprising a GLP-1 agonist and a salt of N-(8-(2-hydroxybenzoyl)amino)caprylic acid, wherein the amount of said salt of N-(8-(2-hydroxybenzoyl)amino)caprylic acid is at least 0.8 mmol.

Form of Composition

3. A composition according to any one of the preceding embodiments, wherein said composition is in the form of a tablet.
4. A composition according to any one of the preceding embodiments, wherein the tablet has a weight in the range of 175-1000 mg.
5. A composition according to any one of the preceding embodiments, wherein the tablet has a weight in the range of 200-800 mg.
6. A composition according to any one of the preceding embodiments, wherein the tablet has a weight selected from the group consisting of 200 mg, such as 400 mg or 700 mg.
7. A composition according to any one of the preceding embodiments, wherein the tablet has a weight selected from the group consisting of 200 mg, 400 mg, 600 mg or 800 mg.

Salt of N-(8-(2-hydroxybenzoyl)amino)caprylic acid

8. A composition according to any one of the preceding embodiments, wherein said salt of N-(8-(2-hydroxybenzoyl)amino)caprylic acid comprises one monovalent cation, two monovalent cations or one divalent cation.
9. A composition according to any one of the preceding embodiments, wherein said salt of N-(8-(2-hydroxybenzoyl)amino)caprylic acid is selected from the group consisting of the sodium salt, potassium salt and calcium salt of N-(8-(2-hydroxybenzoyl)amino)caprylic acid.
10. A composition according to any one of the preceding embodiments, wherein said salt of N-(8-(2-hydroxybenzoyl)amino)caprylic acid is sodium N-(8-(2-hydroxybenzoyl)amino)caprylate (SNAC).

Amount of Salt of N-(8-(2-hydroxybenzoyl)amino)caprylic acid

11. A composition according to any one of the preceding embodiments, wherein the amount of said salt of N-(8-(2-hydroxybenzoyl)amino)caprylic acid is in the range of 0.6-2.1 mmol, such as 0.6-1.9 mmol, 0.7-1.7 mmol or 0.8-1.3 mmol.
12. A composition according to any one of the preceding embodiments, wherein the amount of said salt of N-(8-(2-hydroxybenzoyl)amino)caprylic acid is at least 0.6 mmol, such as selected from the group consisting of at least 0.65 mmol, at least 0.7 mmol, at least 0.75 mmol, at least 0.8 mmol, at least 0.8 mmol, at least 0.9 mmol, at least 0.95 mmol and at least 1 mmol.
13. A composition according to any one of the preceding embodiments, wherein the amount of said salt of N-(8-(2-hydroxybenzoyl)amino)caprylic acid is up to 2.1 mmol, such as selected from the group consisting of up to 2.1 mmol, up to 2 mmol, up to 1.9 mmol, up to 1.8 mmol, up to 1.7 mmol, up to 1.6 mmol, up to 1.5 mmol, up to 1.4 mmol, up to 1.3 mmol, up to 1.2 mmol and up to 1.1 mmol.
14. A composition according to any one of the preceding embodiments, wherein the amount of said salt of N-(8-(2-hydroxybenzoyl)amino)caprylic acid is 1 mmol, such as 1.08 mmol.
15. A composition according to any one of the preceding embodiments, wherein said composition comprises at least 60% (w/w), such as at least 70% (w/w) or at least 75% (w/w), of said salt of N-(8-(2-hydroxybenzoyl)amino)caprylic acid.

Amount of SNAC

16. A composition according to embodiment 10, wherein the amount of SNAC is at least 175 mg, such as an amount selected from the group consisting of at least 200 mg, at least 210 mg, at least 220 mg, at least 230 mg, at least 240 mg, at least 250 mg, at least 260 mg, at least 270 mg and at least 280 mg.
17. A composition according to embodiment 10, wherein the amount of SNAC is up to 575 mg, such as an amount selected from the group consisting of up to 550 mg, up to 525 mg, up to 500 mg, up to 475 mg, up to 450 mg, up to 425 mg, up to 400 mg, up to 375 mg, up to 350 mg and up to 325 mg.

18. A composition according to embodiment 10, wherein the amount of SNAC is 300 mg.

GLP-1

19. A composition according to any one of the preceding embodiments, wherein the amount of the GLP-1 agonist is in the range of 0.01 mg to 100 mg.

20. A composition according to any one of the preceding embodiments, wherein the GLP-1 agonist comprises one substituent.

21. A composition according to any one of the preceding embodiments, wherein said substituent comprises a fatty acid or a fatty diacid.

22. A composition according to any one of the preceding embodiments, wherein said substituent comprises a C16, C18 or C20 fatty acid.

23. A composition according to any one of the preceding embodiments, wherein said substituent comprises a C16, C18 or C20 fatty diacid.

24. A composition according to any one of the preceding embodiments, wherein said substituent comprises formula (X)

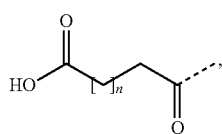

wherein n is at least 13, such as n is 13, 14, 15, 16, 17, 18 or 19.

25. A composition according to any one of the preceding embodiments, wherein said substituent comprises one or more 8-amino-3,6-dioxaoctanoic acid (OEG), such as two OEG.

26. A composition according to any one of the preceding embodiments, wherein the GLP-1 agonist is GLP-1(7-37), GLP-1(7-36)amide, exendin-4 or an analogue thereof comprising up to 10 substitutions, deletions, additions and/or insertions, wherein said GLP-1 agonist optionally comprises one substituent.

27. A composition according to any one of the preceding embodiments, wherein the GLP-1 agonist is GLP-1(7-37), GLP-1(7-36)amide, exendin-4 or an analogue thereof comprising up to 7 substitutions, deletions, additions and/or insertions, wherein said GLP-1 agonist optionally comprises one substituent.

28. A composition according to any one of the preceding embodiments, wherein the GLP-1 agonist is GLP-1(7-37), GLP-1(7-36)amide, exendin-4 or an analogue thereof comprising up to 4 substitutions, deletions, additions and/or insertions, wherein said GLP-1 agonist optionally comprises one substituent.

29. A composition according to any one of the preceding embodiments, wherein the GLP-1 agonist is GLP-1(7-37), GLP-1(7-36)amide, exendin-4 or an analogue thereof comprising up to 3 substitutions, deletions, additions and/or insertions, wherein said GLP-1 agonist optionally comprises one substituent.

30. A composition according to any one of the preceding embodiments, wherein the GLP-1 agonist is semaglutide.

31. A composition according to any one of the preceding embodiments, wherein the amount of the GLP-1 agonist is in the range of 1 to 20 mg, such as in the range of 5 to 20 mg, such as in the range of 5 to 15 mg, such as 10 mg.

32. A composition according to any one of the preceding embodiments, wherein the amount of GLP-1 is in the range of 0.05 to 25 µmol, such as in the range of 0.5 to 2.5 µmol.

Further Excipients

33. A composition according to any one of the preceding embodiments, wherein said composition comprises at least one additional pharmaceutically acceptable excipient.

34. A composition according to any one of the preceding embodiments, wherein said excipient is selected from one or more from the group consisting of binders, fillers, disintegrants and lubricants and/or glidants.

35. A composition according to any one of the preceding embodiments, wherein said composition comprises 0.1-10% (w/w), such as 0.2-4% (w/w) or 0.5-3% (w/w), of binder.

36. A composition according to any one of the preceding embodiments, wherein said composition comprises 1% (w/w) or 2% (w/w) of binder.

37. A composition according to any one of the preceding embodiments, wherein said binder is povidone.

38. A composition according to any one of the preceding embodiments, wherein said composition comprises 5-40% (w/w), such as 10-30% (w/w) or 5-25% (w/w), of filler.

39. A composition according to any one of the preceding embodiments, wherein said composition comprises 10.9% (w/w) or 18%(w/w) of filler, or comprises 19.5% (w/w) or 20.5 (w/w) of filler.

40. A composition according to any one of the preceding embodiments, wherein said filler is avicel, such as avicel PH 102 or avicel PH 200.

41. A composition according to any one of the preceding embodiments, wherein said composition comprises 0.1-10% (w/w) or 0.5-5% (w/w) lubricant and/or a glidant.

42. A composition according to any one of the preceding embodiments, wherein said composition comprises 1-3.5% (w/w) or 1% (w/w) lubricant and/or a glidant.

43. A composition according to any one of the preceding embodiments, wherein said excipient is magnesium stearate.

44. A composition according to any one of the preceding embodiments, wherein said composition comprises at least 60% (w/w) delivery agent, less than 10% (w/w) binder, 5-40% (w/w) filler, and less than 10% (w/w) lubricant and/or glidant.

Administration Regime

45. Use of a composition according to any one of the preceding embodiments, wherein the composition is administered orally.

Functional Features

46. A composition according to any one of the preceding embodiments, wherein said tablet has surface eroding properties.

47. A composition according to any one of the preceding embodiments, wherein said tablet has co-release of the GLP-1 agonist and the delivery agent as determined by the concurrent release test described herein.

48. A composition according to any one of the preceding embodiments, wherein said tablet has a disintegration time in the range of 7-15 minutes as determined by the disintegration test described herein.

49. A composition according to any one of the preceding embodiments, wherein said tablet has a hardness of at least 50 N as determined by the hardness test described herein.

Use as a Medicament
50. Use of a composition as defined in any one of the preceding embodiments in medicine.
51. Use of a composition as defined in any one of the preceding embodiments for treatment of type 2 diabetes or obesity.
52. A method for the treatment of type 2 diabetes or obesity comprising administering a composition as defined in any one of the preceding embodiments.

EXAMPLES

Example 1

The objective of the present study was to evaluate the oral bioavailability in beagle dogs of a series of compositions comprising semaglutide and SNAC.
Method
Animals, Dosing and Blood Sampling
Twenty four male and 24 female beagle dogs, weighing 6-11 kg during the study period were included in the study. The dogs were dosed in fasting state. The compositions were administered by a single oral dosing to the dogs in groups of 4 male and 4 females. Blood samples were taken at the following time points: predose, 0.25, 0.5, 0.75, 1, 1.5, 2, 2.5, 3, 4, 6, 8, 24, 48, 72, 96, 120, 144, 192 and 240 hours post dosing.
The i.v. solution (20 nmol/mL in a pH 7.4 solution comprising 0.1 mg/ml Tween 20, 5.5 mg/ml Phenol, 1.42 mg/ml Na2HPO4 and 14 mg/ml Propylene Glycol) was dosed in a dose volume of 0.1 mL/kg in the same dog colony in one dosing group (n=8). Blood samples were taken at the following time points: predose, 0.25, 0.5, 0.75, 1, 1.5, 2, 2.5, 3, 4, 6, 8, 24, 48, 72, 96, 120, 144, 192 and 240 hours post dosing.
Preparation of Plasma
All blood samples were collected into test tubes containing EDTA for stabilisation and kept on ice until centrifugation. Plasma was separated from whole blood by centrifugation and the plasma was stored at −20° C. or lower until analysis.
Analysis of Plasma Samples
The plasma was analyzed for semaglutide using a Luminescence Oxygen Channeling Immunoassay (LOCI). The LOCI assay employs donor beads coated with streptavidin and acceptor beads conjugated with a monoclonal antibody binding to a midmolecular region of semaglutide. The other monoclonal antibody, specific for an N-terminal epitope, was biotinylated. In the assay the three reactants were combined with the semaglutide which form a two-sited immuno-complex. Illumination of the complex releases singlet oxygen atoms from the donor beads which channels into the acceptor beads and trigger chemiluminescence which was measured in the EnVision plate reader. The amount of light was proportional to the concentration of semaglutide and the lower limit of quantification (LLOQ) in plasma was 100 μM.
Analysis of Compositions
The amount of semaglutide and SNAC in the composition were assayed using a reversed-phase HPLC method, with UV detection at 230 nm, a linear gradient of mobile phases made up of deionised H2O:trifluoroacetic acid (TFA) (1000:1) (v/v) (A), and acetonitrile:TFA (1000:1) (v/v) (B).
Pharmacokinetic Calculations
Semaglutide plasma concentration data were subjected to non-compartmental pharmacokinetic analysis using the PC based software WinNonlin, v. 5.2 (Pharsight, Mountain View, Calif. 94041, U.S.A.). For each individual dog the maximum plasma concentration ($C_{max}$) and time for maximum plasma concentration ($t_{max}$) were read from the plasma concentration time curves. The following pharmacokinetic parameters were estimated: Area Under the Curve to infinity (AUCinf.), and AUCinf./Dose (AUCinf./D). Bioavailability (F) was calculated as the fraction absorbed (in %) based on the dose normalised AUC (AUCinf./D) following oral and intravenous administration. Summary statistics of pharmacokinetic results were presented as arithmetic mean with calculated standard deviation, also for $T_{max}$ and plasma half life.
Preparation of Compositions
Tablets with different amounts of SNAC (150, 300 and 600 mg) and semaglutide (5, 10, 15 and 20 mg) were prepared. The composition of the tablets is shown in Table 1.

TABLE 1

Tablet composition expressed as "per tablet"

| Composition | | A | B | C | D | E | F |
|---|---|---|---|---|---|---|---|
| Semaglutide (mg) | | 10 | 10 | 10 | 5 | 15 | 20 |
| SNAC (mg) | | 150 | 300 | 600 | 300 | 300 | 300 |
| Povidone (mg) | | 2 | 4 | 7 | 3.5 | 4 | 4 |
| Extra-granular | Avicel PH 102 (mg) | 36 | 82 | 76 | 38 | 77 | 72 |
| | Magesium Stearate (mg) | 2 | 4 | 7 | 3.5 | 4 | 4 |
| Tablet Weight (mg) | | 200 | 400 | 700 | 350 | 400 | 400 |

Semaglutide was prepared according to the method described in WO2006/097537, Example 4, and subsequently freeze-dried. SNAC was prepared according to the method described in WO2008/028859. The compositions were prepared using the following manufacturing process:
1) The ingredients were first screened through a #35 mesh;
2) semaglutide and SNAC were geometrically blended in a mortar and pestle;
3) povidone was dissolved in water and the resulting solution was used to granulate the blend of semaglutide and SNAC;
4) the granules were dried at a temperature not exceeding 40° C. to a moisture level of ≤4%; and
5) the resulting dried granules were milled through a #35 mesh;
6) finally, the granules were blended with the extra granular ingredients (see Table 1) and the final blend was compressed into tablets, wherein the compression was performed at a pressure of approximately 4.4 kN or higher.
The tablet hardness of was more than 50 N as determined by the Pharma Test (33AA02), which measures the force required to disrupt the tablet, and the test is based on the pharmacopeia method Ph Eur 2.9.8.
Results
Table 2 summarises the pharmacokinetic parameters for semaglutide from single dosing of the tablets shown in Table 1.

TABLE 2

Summary of pharmacokinetic parameters for semaglutide from single dosing of tablets comprising 10 mg semaglutide in combination with 150 mg (A), 300 mg (B) or 600 mg (C) SNAC.

| Composition | SNAC (mg) | $T_{max}$ (h) | $C_{max}$ (pM) | AUCinf./D | F (%) |
|---|---|---|---|---|---|
| A | 150 | 0.6 | 6222 | 0.62 | 0.17 |
| B | 300 | 0.8 | 21871 | 2.335 | 0.63 |
| C | 600 | 1.1 | 9972 | 1.09 | 0.29 |

Individual and mean (SD) calculated pharmacokinetic parameters following oral dosing appear from Tables 3 to 5 and following intravenous administration appear from Table 6.

TABLE 3

Pharmacokinetic parameters for semaglutide following oral dosing of oral dosing of the combination of 10 mg semaglutide and 150 mg SNAC (Composition A) to 4 male and 4 female Beagle dogs.

| Dog no | Dose (nmol/kg) | $T_{max}$ (h) | $C_{max}$ (pM) | AUCinf./D (h * kg * pmol/l/pmol) | F (%) |
|---|---|---|---|---|---|
| 1025 | 285 | 1.5 | 38300 | 4.08 | 1.1 |
| 1026 | 548 | n.a. | 0 | 0 | 0 |
| 1027 | 278 | 0.2 | 228 | 0 | 0.00003 |
| 1028 | 338 | 2.0 | 3410 | 0.31 | 0.08 |
| 1029 | 246 | n.a. | 0 | 0 | 0 |
| 1030 | 244 | 0.2 | 2030 | 0.07 | 0.02 |
| 1031 | 223 | n.a. | 0 | 0 | 0 |
| 1032 | 254 | 0.5 | 5810 | 0.47 | 0.13 |
| Mean | 302 | 0.6 | 6222 | 0.62 | 0.17 |
| SD | 105 | 0.5 | 13130 | 1.41 | 0.38 | n.a. not analysed

TABLE 4

Pharmacokinetic parameters for semaglutide following oral dosing of oral dosing of the combination of 10 mg semaglutide and 300 mg SNAC (Composition B) to 4 male and 4 female Beagle dogs.

| Dog no | Dose (nmol/kg) | $T_{max}$ (h) | $C_{max}$ (pM) | AUCinf./D (h * kg * pmol/l/pmol) | F (%) |
|---|---|---|---|---|---|
| 1033 | 294 | 0.5 | 5540 | 0.35 | 0.09 |
| 1034 | 301 | 2.0 | 72000 | 6.83 | 1.8 |
| 1035 | 276 | n.a. | 0 | 0 | 0 |
| 1036 | 258 | 1.5 | 21100 | 2.52 | 0.68 |
| 1037 | 239 | 2.0 | 70000 | 8.73 | 2.3 |
| 1038 | 261 | 0.7 | 4050 | 0.28 | 0.07 |
| 1039 | 223 | 0.5 | 2010 | 0.07 | 0.02 |
| 1040 | 249 | 0.2 | 271 | 0.00 | 0.0001 |
| Mean | 263 | 0.8 | 21871 | 2.35 | 0.63 |
| SD | 26.7 | 0.5 | 31061 | 3.49 | 0.94 | n.a. not analysed

TABLE 5

Pharmacokinetic parameters for semaglutide following oral dosing of the combination of 10 mg semaglutide and 600 mg SNAC (Composition C) to 4 male and 4 female Beagle dogs.

| Dog no | Dose (nmol/kg) | $T_{max}$ (h) | $C_{max}$ (pM) | AUCinf./D (h * kg * pmol/l/pmol) | F (%) |
|---|---|---|---|---|---|
| 1041 | 262 | n.a. | 0 | 0 | 0 |
| 1042 | 278 | 0.5 | 1890 | 0.52 | 0.14 |
| 1043 | 265 | 3.0 | 261 | 0 | 0.0005 |
| 1044 | 265 | 0.7 | 1270 | 0.02 | 0.01 |
| 1045 | 251 | 1.5 | 48400 | 5.2 | 1.4 |
| 1046 | 285 | 2.0 | 22900 | 2.53 | 0.68 |
| 1047 | 226 | 0.7 | 4100 | 0.4 | 0.11 |
| 1048 | 248 | 0.7 | 953 | 0.01 | 0.004 |
| Mean | 260 | 1.1 | 9972 | 1.09 | 0.29 |
| SD | 18 | 0.5 | 17298 | 1.87 | 0.50 | n.a. not analysed

TABLE 6

Pharmacokinetic parameters for semaglutide following intravenous dosing of 2 nmol/kg semaglutide to 4 male and 4 female Beagle dogs.

| Dog no | Dose (pmol/kg) | $T_{max}$ (h) | $C_{max}$ (pM) | AUCinf./D (h * kg * pmol/l/pmol) |
|---|---|---|---|---|
| 1065 | 1980 | 0.5 | 31400 | 310 |
| 1066 | 1980 | 0.2 | 17400 | 227 |
| 1067 | 1980 | 0.2 | 28300 | 385 |
| 1068 | 1980 | 4.0 | 12900 | 384 |
| 1069 | 1980 | 0.2 | 28300 | 398 |
| 1070 | 1980 | 0.2 | 27400 | 383 |
| 1071 | 1980 | 0.2 | 31000 | 472 |
| 1072 | 1980 | 0.2 | 25700 | 418 |
| Mean | 1980 | 0.8 | 25300 | 372 |
| SD | 0 | 1.3 | 6638 | 73.8 |

TABLE 7

Summary of pharmacokinetic parameters for semaglutide from single dosing of composition comprising 300 mg SNAC in combination with 5, 10, 15 or 20 mg semaglutide.

| Composition | SNAC (mg) | Semaglutide (mg) | $T_{max}$ (h) | $C_{max}$ (pM) | AUCinf./D | F (%) |
|---|---|---|---|---|---|---|
| D | 300 | 5 | 0.5 | 4446 | 1.22 | 0.33 |
| B | 300 | 10 | 0.8 | 21871 | 2.33 | 0.63 |
| E | 300 | 15 | 1.0 | 42612 | 4.61 | 1.2 |
| F | 300 | 20 | 1.3 | 9603 | 5.09 | 1.4 |

TABLE 8

Pharmacokinetic parameters for semaglutide following oral dosing of the combination of 5 mg semaglutide and 300 mg SNAC (Composition D) to 4 male and 4 female Beagle dogs.

| Dog no | Dose (nmol/kg) | $T_{max}$ (h) | $C_{max}$ (pM) | AUCinf./D (h * kg * pmol/l/pmol) | F (%) |
|---|---|---|---|---|---|
| 1049 | 123 | 1 | 4490 | 1.54 | 0.41 |
| 1050 | 153 | 0.7 | 4420 | 0.5 | 0.13 |
| 1051 | 114 | 1 | 17200 | 4.27 | 1.1 |
| 1052 | 131 | 0.2 | 2390 | 0.52 | 0.14 |
| 1053 | 119 | 0.5 | 1860 | 0.31 | 0.08 |
| 1054 | 131 | 0.2 | 575 | 0.03 | 0.01 |
| 1055 | 113 | 0.7 | 3210 | 0.45 | 0.12 |
| 1056 | 107 | 0.5 | 1420 | 2.16 | 0.58 |
| Mean | 124 | 0.5 | 4446 | 1.22 | 0.33 |
| SD | 15 | 0.5 | 5335 | 1.42 | 0.38 |

TABLE 9

Pharmacokinetic parameters for semaglutide following oral dosing of the combination of 15 mg semaglutide and 300 mg SNAC (Composition E) to 6 Beagle dogs.

| Dog no | Dose (nmol/kg) | $T_{max}$ (h) | $C_{max}$ (pM) | AUCinf./D (h * kg * pmol/l/pmol) | F (%) |
|---|---|---|---|---|---|
| 1067 | 318 | 1 | 56500 | 5.18 | 1.4 |
| 1068 | 393 | 1.5 | 61000 | 4.75 | 1.3 |
| 1069 | 322 | 1 | 15100 | 1.23 | 0.3 |
| 1070 | 341 | 0.5 | 2090 | 0 | 0.01 |
| 1071 | 283 | 2.5 | 114000 | 16.00 | 4.3 |
| 1072 | 312 | 0.5 | 6980 | 0.47 | 0.1 |
| Mean | 328 | 1.0 | 42612 | 4.61 | 1.2 |
| SD | 37 | 0.8 | 43118 | 6.00 | 1.6 |

TABLE 10

Pharmacokinetic parameters for semaglutide following oral dosing of the combination of 20 mg semaglutide and 300 mg SNAC (Composition F) to 4 male and 4 female Beagle dogs.

| Dog no | Dose (nmol/kg) | $T_{max}$ (h) | $C_{max}$ (pM) | AUCinf./D (h * kg * pmol/l/pmol) | F (%) |
|---|---|---|---|---|---|
| 1057 | 588 | 1 | 197000 | 9.60 | 2.6 |
| 1058 | 619 | 1.5 | 144000 | 7.11 | 1.9 |
| 1059 | 508 | 1.5 | 77400 | 4.45 | 1.2 |
| 1060 | 519 | 1.5 | 91900 | 5.18 | 1.4 |
| 1061 | 519 | 2 | 70400 | 4.72 | 1.3 |
| 1062 | 519 | 1.5 | 155000 | 9.09 | 2.4 |
| 1063 | 460 | 0.7 | 1620 | 0.01 | 0.004 |
| 1064 | 487 | 1.5 | 11500 | 0.61 | 0.16 |
| Mean | 527 | 1.3 | 93603 | 5.09 | 1.4 |
| SD | 52 | 0.5 | 68667 | 3.52 | 0.95 |

Conclusion

Surprisingly, tablets comprising 300 mg SNAC showed improved bioavailability in the current study compared to tablets comprising 150 mg or 600 mg SNAC.

---

---

The invention claimed is:

1. A solid composition for oral administration comprising a GLP-1 agonist and a salt of N-(8-(2-hydroxybenzoyl) amino)caprylic acid, wherein
the amount of said salt of N-(8-(2-hydroxybenzoyl)amino) caprylic acid is in the range of 0.8-1.3 mmol, and the GLP-1 agonist is N-epsilon26-[2-(2-{2-[2-(2-{2-[(S)-4-carboxy-4-(17-carboxyheptadecanoylamino) butyrylamino] ethoxy} ethoxy)acetylamino] ethoxy} ethoxy) acetyl] [Aib8, Arg34] GLP-1(7-37).

2. The composition according to claim 1, wherein said composition is in the form of a tablet.

3. The composition according to claim 1, wherein the amount of the GLP-1 agonist is in the range of 5 to 20 mg.

4. The composition according to claim 1, wherein said salt of N-(8-(2-hydroxybenzoyl) amino)caprylic acid is selected from the group consisting of the sodium salt, potassium salt and calcium salt of N-(8-(2-hydroxybenzoyl)amino)caprylic acid.

5. The composition according to claim 4, wherein the amount of the GLP-1 agonist is in the range of 5 to 20 mg.

6. The composition according to claim 4, wherein said salt of N-(8-(2-hydroxybenzoyl) amino)caprylic acid is sodium N-(8-(2-hydroxybenzoyl)amino)caprylate (SNAC).

7. The composition according to claim 6, wherein the amount of the GLP-1 agonist is in the range of 5 to 20 mg.

8. A method for treatment of type II diabetes or obesity comprising administering a composition according to claim 1 to a patient in need thereof.

9. A solid composition for oral administration comprising a GLP-1 agonist and a salt of N-(8-(2-hydroxybenzoyl) amino)caprylic acid, wherein the amount of said GLP-1 agonist is in the range of from 5 to 20 mg, and the GLP-1 agonist is N-epsilon26-[2-(2-{2-[2-(2-{2-[(S)-4-carboxy-4-(17-carboxyheptadecanoylamino) butyrylamino]ethoxy}ethoxy)acetylamino]ethoxy}ethoxy)acetyl][Aib8, Arg34]GLP-1(7-37).

10. The composition according to claim 9, wherein said salt of N-(8-(2-hydroxybenzoyl)amino)caprylic acid is selected from the group consisting of the sodium salt, potassium salt and calcium salt of N-(8-(2-hydroxybenzoyl)amino)caprylic acid.

11. The composition according to claim 10, wherein said salt of N-(8-(2-hydroxybenzoyl)amino)caprylic acid is sodium N-(8-(2-hydroxybenzoyl)amino)caprylate (SNAC).

12. The composition according to claim 11, wherein the amount of SNAC is in the range of 250 mg to 400 mg.

13. The composition according to claim 11, wherein the amount of SNAC is 300 mg.

14. The composition according to claim 9, wherein said composition is in the form of a tablet.

15. A method for treatment of type II diabetes or obesity comprising administering a composition according to claim 9 to a patient in need thereof.

16. A solid composition for oral administration comprising a GLP-1 agonist and a salt of N-(8-(2-hydroxybenzoyl)amino)caprylic acid, wherein the amount of said salt of N-(8-(2-hydroxybenzoyl)amino)caprylic acid is in the range of 0.6-2.1 mmol, and the GLP-1 agonist is N-epsilon26-[2-(2-{2-[2-(2-{2-[(S)-4-carboxy-4-(17-carboxyheptadecanoylamino) butyrylamino]ethoxy}ethoxy)acetylamino]ethoxy}ethoxy)acetyl][Aib8, Arg34]GLP-1(7-37), wherein the amount of the GLP-1 agonist is in the range of 5 to 20 mg.

17. The composition according to claim 16, wherein said salt of N-(8-(2-hydroxybenzoyl)amino)caprylic acid is selected from the group consisting of the sodium salt, potassium salt and calcium salt of N-(8-(2-hydroxybenzoyl)amino)caprylic acid.

18. The composition according to claim 17, wherein said salt of N-(8-(2-hydroxybenzoyl)amino)caprylic acid is sodium N-(8-(2-hydroxybenzoyl)amino)caprylate (SNAC).

19. The composition according to claim 18, wherein said composition is in the form of a tablet.

\* \* \* \* \*